United States Patent [19]

Diederichs et al.

[11] Patent Number: 4,523,467
[45] Date of Patent: Jun. 18, 1985

[54] METHOD AND APPARATUS FOR RESONANT SENSING DEVICE

[75] Inventors: Rolf Diederichs, Erfstadt-Bliesheim; Klaus Volkmann, Bergisch-Gladbach, both of Fed. Rep. of Germany

[73] Assignee: Krautkramer-Branson, Inc., Lewistown, Pa.

[21] Appl. No.: 617,921

[22] Filed: Jun. 6, 1984

[30] Foreign Application Priority Data

Aug. 17, 1983 [DE] Fed. Rep. of Germany ....... 3329690

[51] Int. Cl.$^3$ ............................................. G01N 29/00
[52] U.S. Cl. ..................................... 73/573; 73/1 DV; 73/579
[58] Field of Search ...................... 73/1 DV, 579, 573

[56] References Cited

U.S. PATENT DOCUMENTS

| | | | |
|---|---|---|---|
| 3,472,063 | 10/1969 | Branson | 73/573 |
| 3,490,270 | 1/1970 | Kleesattel | 73/579 |
| 3,499,318 | 3/1970 | Bogdanov et al. | 73/579 |
| 3,572,097 | 3/1971 | Kleesattel | 73/579 |
| 3,955,404 | 5/1976 | Bickel et al. | 73/573 |
| 3,958,450 | 5/1976 | Kleesattel | 73/573 |

Primary Examiner—Howard A. Birmiel
Attorney, Agent, or Firm—Ervin B. Steinberg; Philip J. Feig

[57] ABSTRACT

A resonant sensing device for measuring the hardness of a workpiece to be tested includes a diamond tipped rod adapted to be resonant and for determining the hardness of a workpiece to be tested is brought into forced contact with such workpiece. The difference in resonant frequency of the rod between its not-constrained condition and its constrained condition (forced contact) is a measure of the hardness of the workpiece. The present invention describes a circuit wherein during a first time interval an up/down counter accumulates the counts arising from the oscillations of the not-constrained rod. During the ensuing interval of the same duration, the counter counts down the accumulated count responsive to the oscillations of the constrained rod. As the counter reaches the zero count condition, which condition is reached before the expiration of the time interval, the counter becomes coupled to an adjustable frequency calibration oscillator and for the remainder of the interval the counter accumulates counts from the oscillations of the calibration oscillator. At the end of the interval, the accumulated count is a measure of the hardness of the workpiece.

5 Claims, 4 Drawing Figures

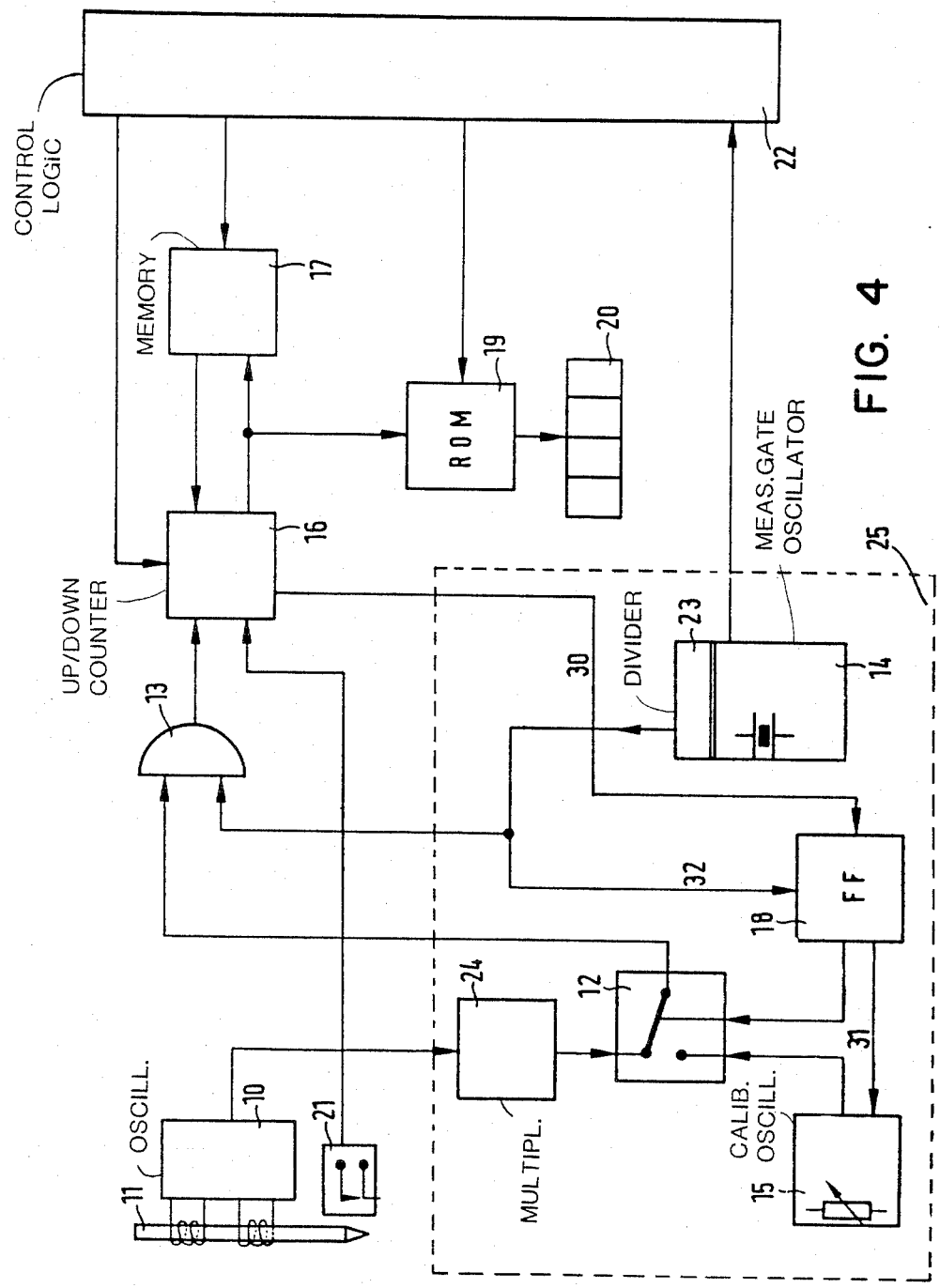

METHOD AND APPARATUS FOR RESONANT SENSING DEVICE

BRIEF SUMMARY OF THE INVENTION

This invention relates to a method and apparatus for measuring the hardness of a workpiece by the impedance contact method wherein a rod is rendered resonant along its longitudinal axis. The oscillations of the rod when not constrained occurring during a first time interval are counted and the oscillations of the same rod when coupled with its front end to a workpiece are counted during a second time interval having the same duration as the first time interval. The difference between the counts is converted to a corresponding hardness value.

Methods and apparatus are known wherein a diamond tipped magnetostrictive or piezoelectric oscillating rod caused to be resonant is coupled to a workpiece under a predetermined engagement force. The difference between the resonant frequency of the rod when oscillating freely, i.e. not constrained, and the resonant frequency when in forced contact with a workpiece is a measure of the workpiece hardness. The principle of this measuring arrangement is described in U.S. Pat. Nos. 3,153,338 issued Oct. 20, 1964 and 3,302,454 issued Feb. 7, 1967, to Claus Kleesattel both entitled "Resonant Sensing Devices". U.S. Pat. No. 3,955,404 in the name of Wolf Bickel, et al. issued May 11, 1976, entitled "Resonant Sensing Device" describes an arrangement for making frequency measurements by counting the oscillations of the resonant rod within an adjustable time interval of a measuring gate. The frequency of the not-constrained rod is measured by means of an up/down counter during a time interval determined by the measuring gate and the accumulated count is stored in a memory. The measurement is repeated several times per second. The rod is then coupled to the workpiece whose hardness is to be determined and the up/down counter is pre-set with the contents of the memory. The oscillations of the new resonant frequency when the rod is in contact with the workpiece are counted during a following and identical time interval determined by the measuring gate. A difference between the frequency counts arises due to the fact that the resonant frequency of the rod is higher when coupled to the workpiece than when the rod is oscillating in its not-constrained state. The difference in frequency count is then converted by means of a read-only memory (ROM) to a hardness value and such value is displayed.

The measuring instrument must be calibrated with reference to a calibration block of known hardness. The disadvantage of the latter method resides in the complex and time consuming calibration method. To adjust the measuring instrument, the time interval of the measuring gate must be varied frequently in a number of adjusting steps by adjusting a measuring gate oscillator until the instrument indicates the hardness value corresponding to that of the calibration block. If the indicated hardness value differs from the calibration value, it is necessary to lift the oscillating rod from the calibration block and readjust the measuring gate oscillator without any possibility of determining the effect of this procedure on the hardness value indication. The oscillating rod is then brought back into engagement with the calibration block and the indicated hardness value is read. If the new hardness value is still incorrect, the measuring gate oscillator is adjusted once again with the oscillating rod removed from engagement. This adjustment procedure is repeated until the correct difference value is formed and the measuring instrument indicates the correct hardness value of the calibration block.

The reason for this rather complex calibration adjustment is that when adjusting the measuring gate oscillator, the common time interval for counting the oscillations of the resonant frequency of the rod in the not-constrained and in the constrained condition is altered.

It is an important object of this invention, therefore, to provide a calibration arrangement which is characterized by greater speed and simplicity than the heretofore known arrangements.

It is another important object of this invention to provide a circuit arrangement for the impedance hardness measuring method which provides a simple and straightforward calibration.

Further and other important objects of this invention will be more clearly apparent by reference to the following description when taken in conjunction with the accompanying drawings.

BRIEF DESCRIPTION OF THE FIGURES

FIG. 4 is a schematic electrical circuit diagram similar to FIG. 1 with the addition of a frequency multiplier and a binary divider.

DETAILED DESCRIPTION OF THE INVENTION

Figure 1:
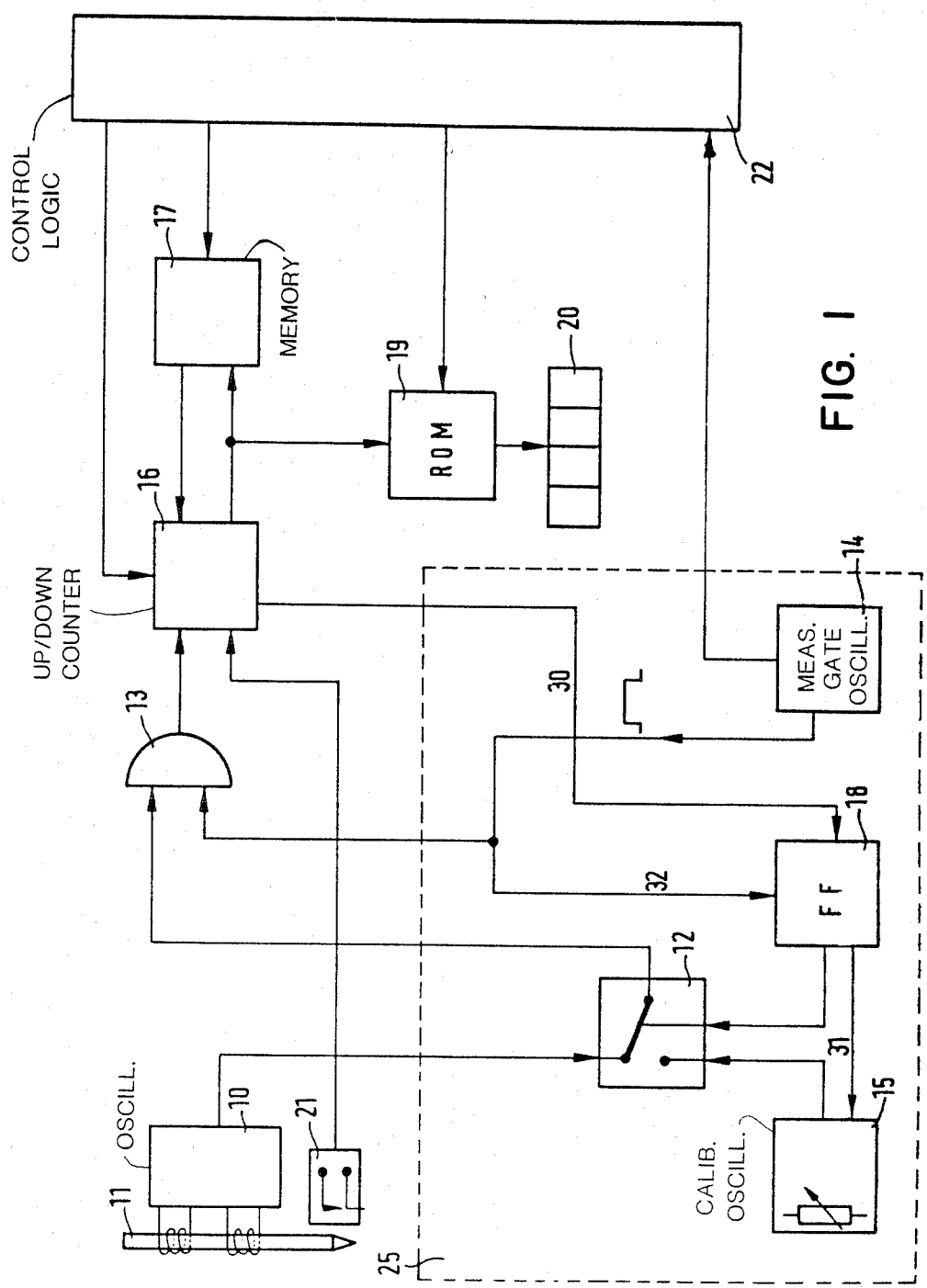
FIG. 1 is a schematic electrical circuit diagram of the present invention including oscillators, switching means and a flip-flop circuit.

Referring now to the figures and FIG. 1 in particular, there is shown a schematic block diagram of the hardness measuring apparatus per the present invention wherein the electrical circuit comprising the improvement is shown within the dashed lines 25. The circuit comprises essentially an electronic switching means 12 which is controlled by a flip-flop 18, a measuring gate oscillator 14 for producing a time interval t1 during which oscillations are counted and an adjustable calibration oscillator 15, the operation of which is started and stopped by flip-flop 18 via conductor 31. Also shown in FIG. 1 is the heretofore known impedance hardness measuring device comprising a rod 11 which can be coupled with its diamond tipped front end to a workpiece under a predetermined engagement force. An energizing or exciting circuit 10 causes the rod 11 to become resonant along its longitudinal axis. The resulting resonant oscillations and the pulse for the time gate t1 are fed through an AND gate 13, the output of which is connected to an up/down counter 16. A sensing switch 21 supplies a signal to the counter 16 when the rod is in forced contact with the workpiece. A memory 17 is coupled to the output from the counter 16. A read-only memory 19, coupled to a digital display 20, is coupled to the output of the counter 16. A control logic 22 provides the proper timing for causing the functions to occur in the predetermined manner.

Figure 2:
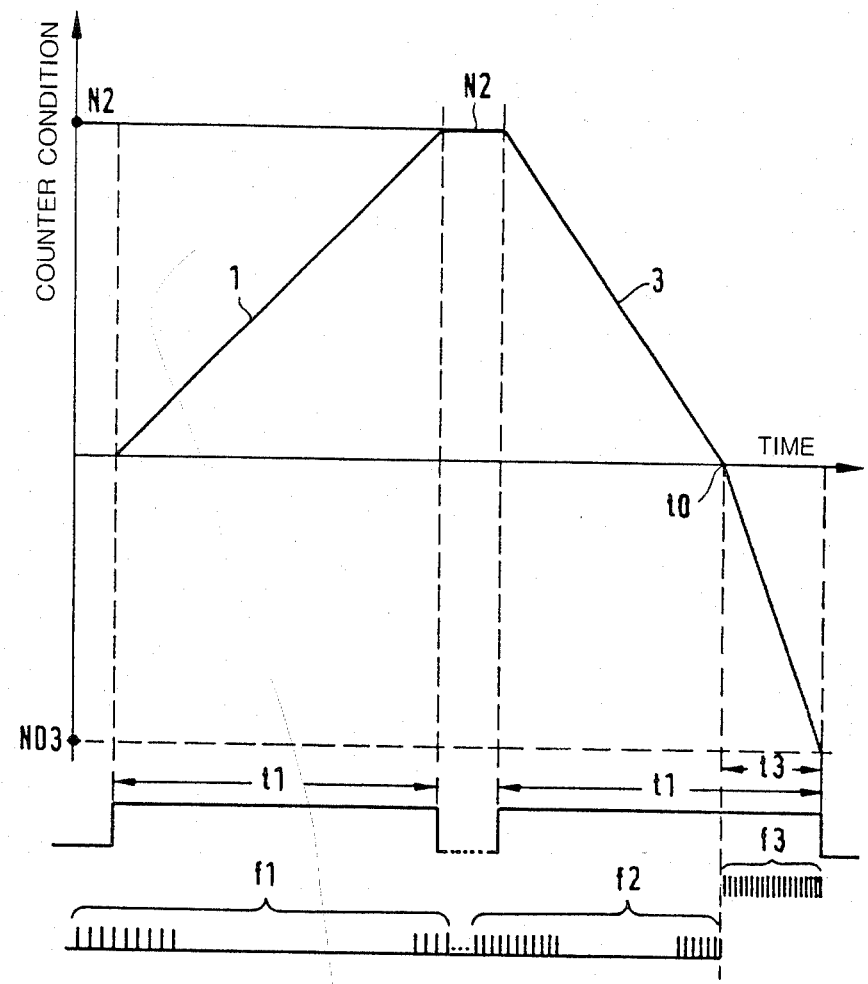
FIG. 2 is an illustration depicting the time responsive change of the counter condition, showing also the time interval and count frequencies.

Referring now to FIG. 2, line 1 denotes the state of the counter 16 increasing its accumulated count during the first time interval t1. Line 3 denotes the state of the counter decreasing its accumulated count during a second time interval t1 which is of the same duration as the first time interval. For the sake of simplicity, the two lines 1 and 3 are shown as continuous lines although the state of the counter alters stepwise. The counter 16 has attained the count state N2 between the first and the second time intervals. The rod 11 oscillates, when free of contact with a workpiece, at a frequency f1 and, when in forced engagement with a workpiece at a frequency f2. The adjustable frequency oscillator 15, FIG. 1, used for calibration purposes, operates at a frequency f3.

Determining the hardness of a workpiece in accordance with the present invention utilizing the operation of the circuit disclosed hereinbefore will now be described with reference to FIGS. 1 and 2. In hardness measuring instruments of the present kind, the rod 11 is caused to resonate at the frequency f1 by the exciting circuit 10 which includes a feedback arrangement. It will be assumed at the present moment that rod 11 is free of contact with a workpiece. Within a preferably fixed, that is non-adjustable, time interval t1 which is determined by the fixedly adjusted measuring gate oscillator 14, the counter 16 counts up responsive to the oscillations of the resonant frequency f1 (line 1 in FIG. 2). Upon the termination of the interval t1 counting ceases and the accumulated count N2 is transferred to the memory 17 and the counter 16 is reset. This counting procedure is repeated several times per second. Therefore, at all times the most recent actual count value is stored. Changes in the resonant frequency caused by changes in temperature or other influences causing a frequency shift are continuously taken into account.

When the rod 11 is now placed in contact with a workpiece, a signal given by the switch 21 causes the counter 16 to be set to the most recent count N2 derived from the memory 17. At the start of the ensuing, that is, second time interval t1, the counter 16 now counts downward in response to the oscillations of the resonant frequency f2 (line 3), the latter frequency being higher on account of the rod being coupled to the workpiece, that is being constrained. During the latter interval t1 there is a passage of the counter 3 through zero at a time t0 (0<t0<t1). As the counter passes through zero, the counter 16 provides a pulse via conductor 30 to flip-flop 18 which changes the state of the switching means 12. The switching means disconnects the exciting circuit 10 and connects the adjustable calibration oscillator 15 via gate 13 to the counter 16. Consequently, in accordance with the present invention, the oscillations from the oscillator 15 are counted for the remaining time interval t3=t1−t0.

Hence, a count difference ND3 is developed at the end of the latter time interval t1. The value ND3 is converted by the read-only memory 19 to a hardness value and is displayed at the digital display 20. This counting operation is repeated several times a second for as long as the rod 11 remains in forced contact with the workpiece. In order to start the calibration oscillator 15 it is advantageous that flip-flop 18 via conductor 32 responsive to the trailing edge of the measuring gate at the end of the time interval t1 changes over to its normalized state and responsive to the zero pulse from the counter 16 via line 30 changes over into its operative state. Upon change over from its normalized state to its operative state, the flip-flop 18 starts the calibration oscillator 15 via conductor 31 simultaneously, that is, at the time t0. The advantage of this feature compared with continuously oscillating oscillators is that the calibration oscillator can be phase-lock synchronized by known synchronization methods.

This invention permits a rapid calibration of the hardness measuring device. For calibration, the rod 11 is placed on a calibration block having a known hardness and the frequency f3, that is, the period 1/f3 of the oscillations of the adjustable calibration oscillator 15 are varied to give the correct value ND3, which upon conversion by the read-only memory 19 causes the digital display 20 to display the correct hardness value.

Figure 3:
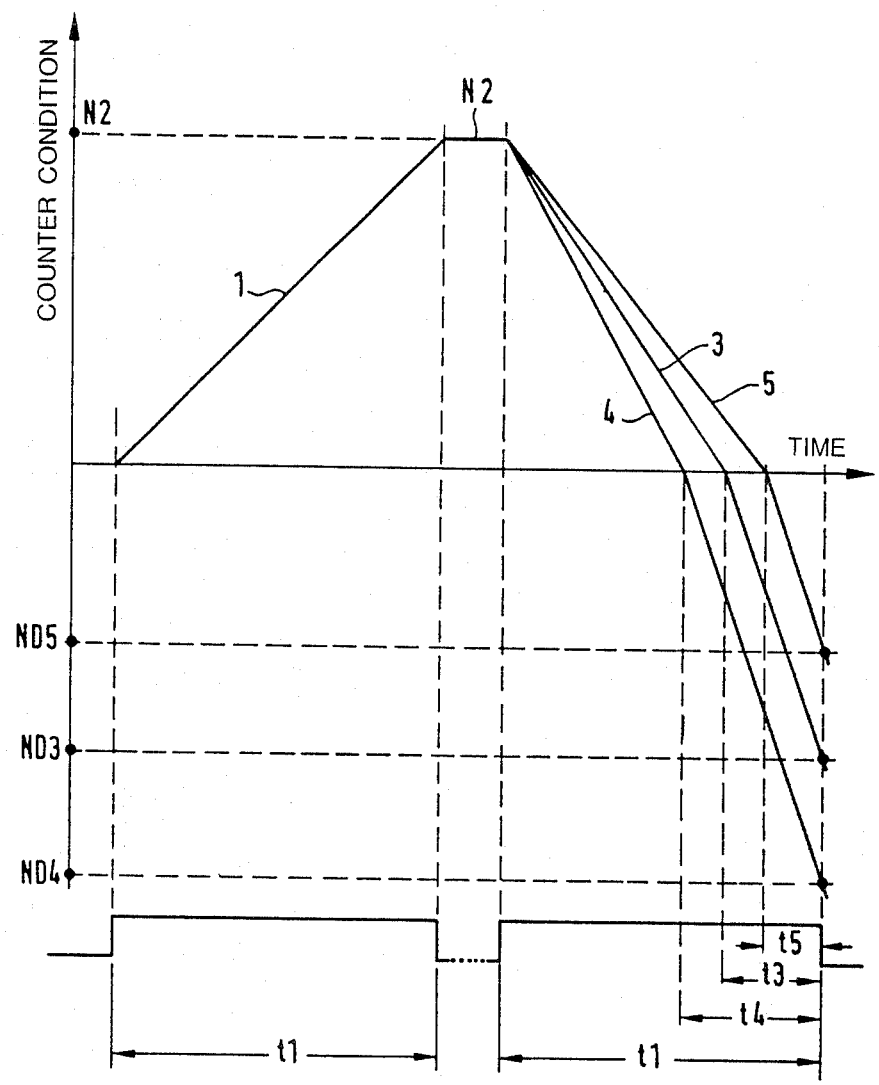
FIG. 3 is an illustration depicting the different counter conditions as a function of the hardness of a workpiece.

The hardness measurement will be described hereinafter with reference to FIG. 3. After completing the calibration procedure, the oscillating rod 11 is brought into contact with the workpiece. The accumulated count N2 responsive to the oscillations of the not-constrained condition of the rod 11 is contained in the memory 17. If the workpiece is softer than that of the calibration block, the resonant frequency of the rod will be higher, for instance a value f4 (f4>f2). Hence, during counting the "null difference" is achieved earlier than during the calibration procedure (line 4). The remaining time interval t4 is counted using the oscillations from the calibration oscillator 15 adjusted during the calibration procedure and resulting in the count difference ND4.

If, however, the workpiece measured by the rod 11 is harder, using the same considerations, line 5 is obtained assuming f5<f2. The count difference will be ND5. As stated previously, the difference values are converted to hardness values by the read-only memory.

For the sake of accuracy it is advantageous that the oscillations to be counted in respect of their frequencies be of substantially the same magnitude. To this end, and as shown in FIG. 4, the resonant frequencies of the rod f1 and f2 are multiplied, for instance doubled, for counting using a frequency multiplier 24. In an example used, the resonant frequencies are 78.00 kHz and 78.50 kHz respectively, and then doubled for counting during the time interval t1 to 156.0 kHz and 157.0 kHz respectively. Advantageously, the time interval t1 of 355 milliseconds, for instance, is produced by a crystal oscillator (for instance 1.8 MHz) and brought to 355 milliseconds by a binary divider 23. Consequently, within this time interval of 355 ms applicable to the not-constrained rod condition 55,380 oscillations are counted, whereas for the constrained condition (157.0 kHz) the passage through zero occurs at:

$$t0 = \frac{1}{157 \times 10^3/s} \times 55{,}380 = 352.74 \text{ ms.}$$

In the remaining time interval t3=2.26 ms the oscillations 1/f3 from the calibration oscillator 15 whose frequency f3 is adjustable, are counted, the oscillator 15 having been so adjusted during the calibration step that after conversion the correct hardness value was displayed.

What is claimed is:

1. A method for testing the hardness of a workpiece by the contact impedance method using an oscillating rod excited at its natural resonant frequency wherein the oscillations of the not-constrained rod are counted during a first time interval and the oscillations of the constrained rod, when in forced contact with the workpiece, are counted during a second time interval having the same duration as said first interval and the difference in counts is converted to a corresponding hardness value, the improvement comprising:

counting the oscillations of said rod when coupled to the workpiece beginning with the start of said second time interval only until the difference between the count during said second time interval and the count of the oscillations of the not-constrained rod during said first time interval becomes zero, and during the remainder of said second time interval counting the number of oscillations obtained from an adjustable frequency oscillator.

2. A method for testing the hardness of a workpiece as set forth in claim 1 and including adjusting the frequency of said adjustable frequency oscillator in such a manner that the count accumulated during the remainder of said second time interval is commensurate with the hardness of the workpiece.

3. A circuit for testing the hardness of a workpiece by the contact impedance method using a rod adapted to be rendered resonant, the difference between the resonant frequency of the rod when not constrained and when constrained in forced contact with the workpiece whose hardness is to be measured being a measure of the hardness, including an oscillator for causing said rod to be resonant and an adjustable measuring gate oscillator, both being coupled to an up/down counter, the improvement comprising:

means coupling said oscillator causing said rod to be resonant by means of a first input of a switching means to a first input of an AND gate whose output is coupled to said up/down counter;

a measuring gate oscillator having a fixedly adjusted frequency coupled to the second input of said AND gate;

an adjustable frequency calibration oscillator coupled to the second input of said switching means;

a flip-flop coupled to said measuring gate oscillator for being set to its normal state by means of a first input and for being set to its actuated state by means of a second input responsive to a predetermined zero count condition of said counter, and means coupling the output of said flip-flop to said switching means and to said adjustable frequency calibration oscillator for causing responsive to said predetermined zero count condition of said counter said flip-flop to change its condition from a normalized condition to an operative condition and in response thereto change the condition of said switching means to cause said counter to accumulate frequency counts from said calibration oscillator for a remaining time interval determined by said measuring gate oscillator.

4. A circuit for testing the hardness of a workpiece as set forth in claim 3 and including a frequency multiplier coupled in series between said oscillator rendering said rod resonant and said switching means.

5. A circuit for testing the hardness of a workpiece as set forth in claim 4, said measuring gate oscillator being a quartz-stabilized oscillator and including a binary frequency divider coupled between said quartz stabilized oscillator and said AND gate.

* * * * *